United States Patent [19]

Soules

[11] Patent Number: 5,744,954

[45] Date of Patent: Apr. 28, 1998

[54] MAGNETIC FIELD GENERATION IN FERROMAGNETIC METAL OBJECTS

[75] Inventor: Jack Arbuthnott Soules, Shaker Heights, Ohio

[73] Assignee: Cleveland State University, Cleveland, Ohio

[21] Appl. No.: 755,785

[22] Filed: Nov. 25, 1996

[51] Int. Cl.⁶ .......................... G01N 27/72; G01R 33/12
[52] U.S. Cl. .................................. 324/234; 324/225
[58] Field of Search .............................. 324/234, 236, 324/237, 225, 207.16, 207.19

[56] References Cited

U.S. PATENT DOCUMENTS 4,847,552  7/1989  Howard ........................... 324/236

Primary Examiner—Walter E. Snow
Attorney, Agent, or Firm—Jane B. Marciniszyn Esq.

[57] ABSTRACT

A novel test method enables physical properties in ferromagnetic metals to be more reliably measured with induced eddy current flow. An adverse Barkhausen effect is prevented during the test measurements to enable detection of extremely small conductivity changes in the particular ferromagnetic metal object being tested.

13 Claims, 1 Drawing Sheet

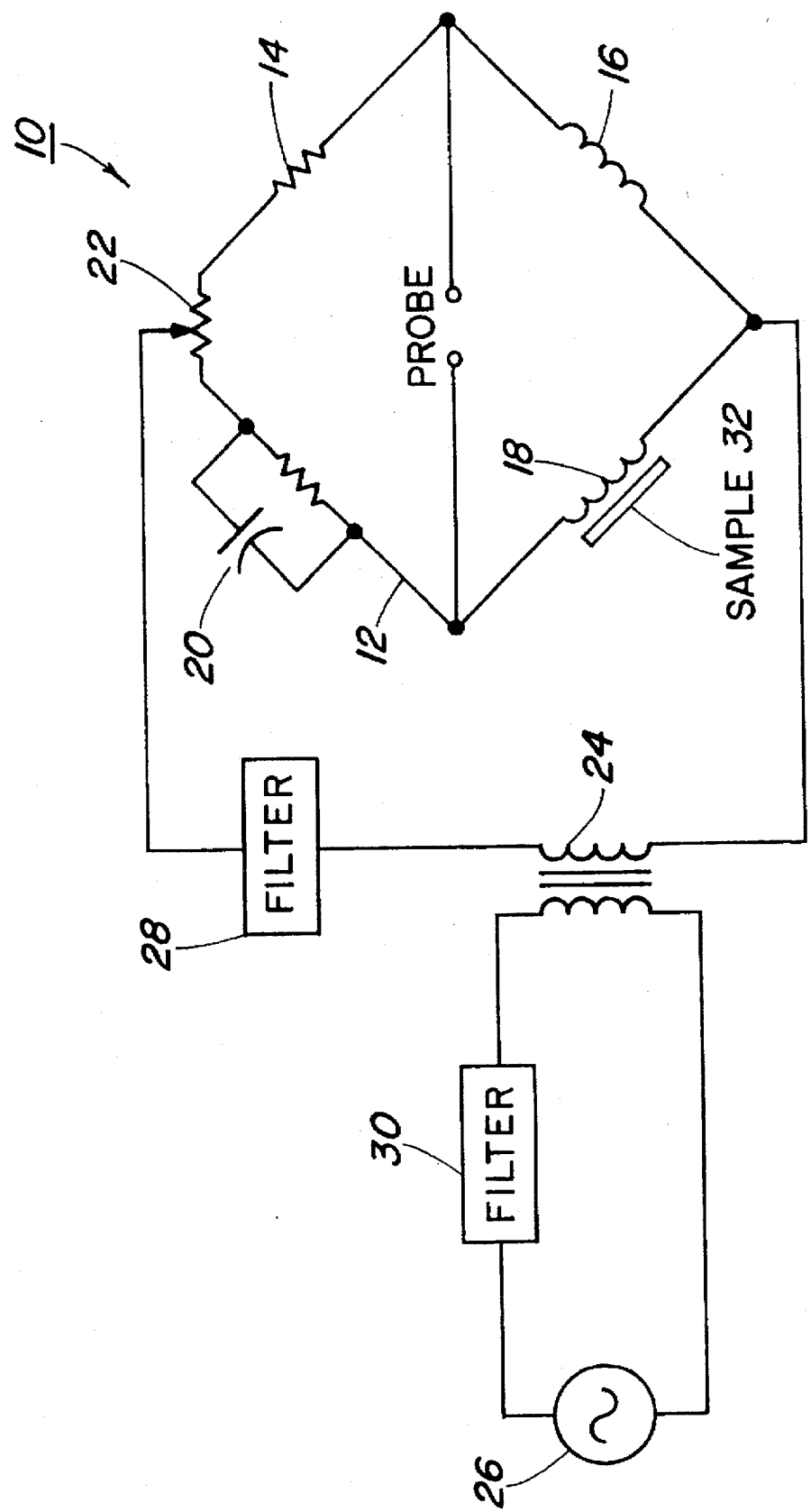

MAGNETIC FIELD GENERATION IN FERROMAGNETIC METAL OBJECTS

BACKGROUND OF THE INVENTION

This invention relates generally to a test method for measurement of existing physical properties in ferromagnetic metal objects and more particularly, to an improved eddy current measurement procedure enabling extremely minor conductivity changes in these metal objects to now be reliably detected.

As a non-destructive test procedure, eddy current measurement has long been employed for detection of relatively macroscopic defects or compositional variation in ferromagnetic metal objects such as surface and sub-surface cracks or flaws, irregularities in material structure and still other variations in the metallurgical characteristics. Existing eddy current technique has enabled detection of such defects with conductivity changes in the metals being tested being limited in sensitivity to about one part in one thousand parts. A far greater sensitivity in the order of one part in one hundred thousands parts is needed, however, for physical property changes produced in metals from both use and treatment. Thus, it is well recognized that a wide variety of physical properties in a metal object will be altered with heat treatment, for example, as well as resulting from fatigue or residual stress. The existing eddy current measurement techniques were thereby found incapable of detecting such smaller conductivity changes in metals in even so called "perfect" metals lacking material or structural imperfections.

In U.S. patent application Ser. No. 08/540,496, entitled "Eddy Current Test Method for Residual Stress in Non-Ferromagnetic Metal Objects", filed Oct. 10, 1995, now U.S. Pat. No. 5,610,515 in the name of the present inventor there is disclosed a novel eddy current measurement technique enabling extremely minor conductivity changes in such metal objects to now be reliably measured. As therein disclosed the residual stress produced in titanium and aluminum alloys, such as near surface compression resulting from mechanical action such as shot peening or rolling can now be reliably detected upon carrying out a structural modification of existing eddy current test equipment. In doing so, a smart Eddy™ system employing software programmed general purpose computer means can be employed which is operatively associated with an alternate current bridge measuring circuit. Required modification of said bridge circuit utilizes resistor elements having relatively low thermal coefficient values being kept isolated at a remote physical location where resistance change with temperature fluctuation is minimal being further employed in combination with a probe device suitable for customary displacement or lift-off measurement procedures. The employed probe device features spaced apart identical test and comparison induction coils suitable for operation in the frequency range from 100 KHz to about 10 MHz, the probe device being constructed so that only the test induction coil in said device physically contacts the surface of the non-ferromagnetic metal object being tested while the comparison induction coil in said probe device remains physically positioned remote therefrom. The so modified test equipment enables a measurement accuracy of at least 5 parts per million for a detection of residual stress in non-ferromagnetic metal objects.

A far more difficult problem exists for employment of eddy current measurement techniques to detect physical property changes in ferromagnetic metals. This problem is called the "Barkhausen effect" as generally defined on pages 339–400 of the text "Electricity and Magnetism", Francis Weston Sears author, published by Edison Wesley Publishing Inc. (1951). The adverse results of this effect is a voltage surge produced in ferromagnetic metals upon domain shift of the magnetizable metal crystals. Thus, ferromagnetic metals respond dynamically whenever individual magnetic domains align with the constantly changing magnetic fields induced by eddy current measurement techniques. The voltage surge produced in this manner ranges in amplitude from microvolts to millivolts hence can generally be ignored for eddy current measure of macroscopic defects, such as cracks and flaws, which produce induced currents exceeding such adverse effect. On the other hand, such effect has been found so far to mask or overpower the far lower induced currents produced with a veritable myriad of physical property changes which frequently occur in ferromagnetic metal objects.

Accordingly, it is an important object of the present invention, therefore, to provide an extremely sensitive eddy current test procedure for measurement of existing physical properties in ferromagnetic metal objects.

It is another important object of the present invention to modify conventional eddy current test equipment in a manner enabling accurate detection of existing physical properties in ferromagnetic metal objects.

It is a still further object of the present invention to significantly increase the detection sensitivity of conventional eddy current test equipment in a simplified manner not requiring extensive modification of its component parts.

These and further important objects of the present invention will become further apparent upon considering the following more detailed description of the present invention.

SUMMARY OF THE INVENTION

It has now been discovered, surprisingly, that extremely sensitive detection of minor conductivity changes in ferromagnetic metal is provided by generating induced currents during the test procedure which do not cause any substantial domain shift in the metal object. In doing so, very small currents are generated with the test equipment to keep the magnetic fields produced by eddy current in the ferromagnetic metal object being tested at a level of $10^{-3}$ Tesla or less. At this field strength the Barkhausen effect does not occur to interfere with the relatively small eddy current being inducted. To analyze the pertubation caused with such small eddy current flow in the ferromagnetic metal object being tested further requires an alternating current bridge circuit having a sufficient degree of sensitivity, such as described in the aforementioned copending U.S. Ser. No. 08/540,496 application. Accordingly, the entire contents of said copending patent application are hereby specifically incorporated by reference into the present application. The probe device suitable for operation with said alternating current bridge circuit is designed with respect to the magnetic "hardness" or "softness" (magnetic permeability) of the particular ferromagnetic metal object being tested. That is, hard ferromagnetic metals require a larger magnetic field to produce the Barkhausen effect than soft ferromagnetic metals. It follows from such consideration that the magnetic field being generated with said probe device according to the present method is kept below that producing any significant Barkhausen interference. A representative probe device constructed in such manner employs identical test and comparison induction coils, the probe device being constructed so that only the test induction coil in said probe device physically contacts the surface of the ferromagnetic metal object being tested while the comparison induction coil in said probe device remains physically positioned remote therefrom.

Basically, the present method entails contacting the surface of the ferromagnetic object being tested with a probe device generating a magnetic field below that causing any substantial domain shift in the metal, having said probe device electrically connected in an alternating current bridge circuit causing current flow in the probe device, balancing the bridge circuit during probe operation, repeating said measurement for a ferromagnetic metal object having the same metallurgical characteristics and comparing the electrical conductivity values detected for the respective ferromagnetic metal objects to determine any differences found therebetween. With such procedure, it now becomes possible to detect conductivity changes as small as 5 parts per million or less in various ferromagnetic metals, such as steel alloys and the like. A representative embodiment for said improved method of measurement comprises (a) contacting the surface of said ferromagnetic metal object with a probe device having spaced apart identical test and comparison induction coils, the probe device being constructed so that only the test induction coil in said probe device physically contacts the surface of the ferromagnetic object being tested while the comparison induction coil in said probe device remains physically positioned remote therefrom, (b) both induction coils in said probe device further being limited in construction so that the electrical output from said test induction coil generates a magnetic field in the ferromagnetic metal object being tested below that causing any substantial domain shift in the metal, (c) the test and comparison coils of said probe device providing bridge arms in an alternating current bridge circuit formed in combination with resistor elements, said resistor elements exhibiting the same resistance characteristics including a relatively low thermal coefficient value, (d) energizing said bridge circuit at an operating frequency suitable for the particular ferromagnetic metal object being tested causing self-inductance eddy current flow in both induction coils of said device while the test induction coil in said probe device remains in physical contact with the surface of said ferromagnetic metal object being test, (e) balancing the bridge circuit during said probe operation, (f) repeating steps (a) through (e) with the probe device at the same operating conditions while employing a ferromagnetic metal object having the same metallurgical characteristics, and (g) comparing the electrical conductivity values detected for the respective ferromagnetic metal objects to determine differences found therebetween.

BRIEF DESCRIPTION OF THE DRAWING

The accompanying drawing is an electrical circuit diagram depicting a representative alternating current bridge circuit suitable for practice of the present method.

DETAILED DESCRIPTION OF THE PREFERRED EMBODIMENTS

Referring to the accompanying circuit diagram, a representative alternating current bridge circuit 10 is depicted found suitable for practice of the present method. The depicted circuit employs four bridge arms 12, 14, 16 and 18 further connected to a suitable probe device (not shown) for generation of a relatively small eddy current in the ferromagnetic metal object being tested. Bridge arms 12 and 14 consist of 500 ohm resistor elements whereas remaining bridge arms 16 and 18 both consist of induction coils having 500 ohm impedance at the chosen test frequency and being further encapsulated in the employed probe device to be more fully described hereinafter. Bridge arm 12 further includes capacitor element 20 to cooperate with an adjustable resistor element 22 as the means to enable balancing of said bridge circuit to a null value. Adjustable resistor element 22 has a resistance range of 0–10 ohms with capacitor element 20 having a 0–10 pfd value. Operation of said bridge circuit is provided with a ferrite transformer 24 coupling the circuit to a power source 26 with low pass filters 28 and 30 further being interconnected as shown to eliminate interference of harmonic drive signals from the particular power source being employed. The RF type transformer device 24 enables circuit operation in the range from 100 KHz to 1 MHz when supplied from a conventional student type RF generator 26 adjustable in the range from 10 KHz to 5 MHz to provide a 0–5 volt output.

A 4140 grade steel alloy sample 32 was tested with the foregoing alternating current bridge circuit when employed in combination with a probe device (unnumbered) designed for operation in the 300 KHz frequency range. Said probe device utilized a pair of spaced apart test and comparison induction coils entirely sealed within an electrically nonconductive jacket, and with said test coil being lodged sufficiently adjacent to the jacket wall for inducing eddy current flow in the metal object being tested upon probe placement in physical contact therewith. A flat test coil was utilized in said probe device for optimum contact with the flat surface of the metal object being tested although other test coil configurations are understandably contemplated with non-flat object surfaces such as gear teeth and the like. Said test coil further required a combination of coil inductance and coil current producing an alternating magnetic field in the particular test sample whose peak value does not exceed $5 \times 10^{-5}$ Tesla in value. In meeting such limitation, the selected test coil of 1 cm diameter utilized 27 turns of #32 copper wire carrying a peak current of approximately 14 milliamperes, or an RMS current of approximately 10 milliamperes. When operated with a driving voltage of up to 5 volts with the herein illustrated bridge circuit, extremely small electrical currents were induced in the test sample causing unbalance of the bridge circuit. A subsequent rebalancing of said bridge circuit with the employed circuit elements enables detection of any minor changes in electrical conductivity of the test sample attributable to its existing physical condition, such as surface stress in the metal adjacent to the test coil position. Such detection can be determined for the herein illustrated example from a comparison with an unstressed steel sample having the same metallurgical characteristics upon repeating the test measurements at the same circuit operating conditions.

To illustrate further practice of the present method employing the modified smart Eddy™ system equipment as described in the aforementioned copending U.S. Ser. No. 08/540,496 application, a shot-peened sample of the same 4140 grade steel alloy was tested to determine the degree of residual stress occurring in the top surface region. In accordance therewith, the above illustrated probe device was positioned in physical contact with the surface of a shot-peened portion of the test sample for automated determination of conductivity values occurring over a range of operating frequencies from about 300 KHz to about 600 KHz. The appropriate frequency is determined by the desired depth of the physical property, that is stress, alloy, heat treatment and so forth to be determined. Repetition of these measurements was then conducted at the same operating conditions with the probe device being positioned in contact with an unpeened surface portion of said test sample to enable a comparison being made with the earlier obtained conductivity values. Such comparison enabled the residual stress found in the tested sample to be determined at various frequencies, using the variation in conductivity which must be measured to a sensitivity of at least 5 parts per million.

It will be apparent from the foregoing description that a broadly useful and novel test method for determining a wide variety of physical properties in ferromagnetic metal objects has been provided now enabling extremely sensitive measurement of the particular physical condition. It can likewise be appreciated that the present method provides improved detection of flaws and still other discontinuities in ferromagnetic metal objects. It is contemplated that such measurement procedure can be employed for a broad range of ferromagnetic metal objects and materials other than specifically illustrated herein, however, to include measurement of metal fatigue as well as physical condition after heat treatment. Likewise, it is contemplated that the herein disclosed test procedure can be carried out with other test equipment employing alternating bridge measuring circuitry than herein illustrated, including both manually operated and automatically operating circuit means. Consequently, it is intended to limit the present invention only by the scope of the appended claims.

What I claim as new and desire to secure by Letters Patent of the United States is:

1. An improved method for measurement of existing physical properties in a ferromagnetic metal object which comprises:
   (a) contacting a surface of said ferromagnetic metal object with a probe device having spaced apart identical test and comparison induction coils,
   (b) both induction coils in said probe device further being limited in construction so that electrical output from said test induction coil generates a magnetic field in said ferromagnetic metal object tested below that causing any substantial domain shift in said metal, wherein said maximum allowable magnetic field may be as large as $10^{-3}$ Tesla in some hard ferromagnetic metal objects and as small as $10^{-5}$ Tesla in very soft ferromagnetic metal objects and wherein limiting said magnitude of said alternating magnetic field prevents the excitation of domain movement and eliminates Barkhausen noise,
   (c) said test and comparison induction coils of said probe device providing bridge arms in an alternating current bridge circuit formed in combination with resistor elements, said resistor elements exhibiting the same resistance characteristics,
   (d) energizing said bridge circuit at an operating frequency suitable for the particular ferromagnetic metal object being tested causing self-inductance eddy current flow in both induction coils of said probe device while said test induction coil in said probe device remains in physical contact with said surface of said ferromagnetic metal object being tested,
   (e) balancing said bridge circuit during said probe operation,
   (f) repeating steps (a) through (e) with said prove device at the same operating conditions while employing a ferromagnetic metal object having the same metallurgical characteristics, and
   (g) comparing electrical conductivity values detected for said respective ferromagnetic metal objects to determine any differences found therebetween.

2. The method of claim 1 whereby residual stress in said ferromagnetic metal object is detected.

3. The method of claim 2 whereby residual surface stress in said ferromagnetic metal object is detected.

4. The method of claim 2 whereby residual surface stress in said ferromagnetic metal object after shot peening is detected.

5. The method of claim 2 whereby residual surface stress in said ferromagnetic metal object after mechanical rolling is detected.

6. The method of claim 1 wherein said ferromagnetic metal object being measured is a ferrous alloy.

7. The method of claim 1 wherein said maximum magnetic field being generated with said probe device depends upon magnetic permeability of said particular ferromagnetic metal object being tested.

8. The method of claim 1 wherein said test induction coil in said probe device is constructed with a surface configuration conforming to said particular surface of said ferromagnetic metal object being tested.

9. An improved method for measurement of existing physical properties in a ferromagnetic metal object which comprises:
   (a) contacting a surface of said ferromagnetic metal object with a probe device having spaced apart identical test and comparison induction coils, said probe device being constructed so that only said test induction coil in said probe device physically contacts said surface of said ferromagnetic metal object being tested while said comparison induction coil in said probe device remains physically positioned remote therefrom,
   (b) both induction coils in said probe device further being limited in construction so that an electrical output from said test induction coil generates a magnetic field in said ferromagnetic metal object being tested below that causing any substantial domain shift in said metal thus eliminating Barkhausen noise,
   (c) said test and comparison induction coils of said probe device providing bridge arms in an alternating current bridge circuit formed in combination with resistor elements, said resistor elements exhibiting the same resistance characteristics including a relatively low thermal coefficient value,
   (d) energizing said bridge circuit at an operating frequency suitable for said particular ferromagnetic metal object being tested causing self-inductance eddy current flow in both induction coils of said probe device while said test induction coil in said probe device remains in physical contact with said surface of said ferromagnetic metal object being tested,
   (e) balancing said bridge circuit during said probe operation,
   (f) repeating steps (a) through (e) with said probe device at the same operating conditions while employing a ferromagnetic metal object having the same metallurgical characteristics, and
   (g) comparing electrical conductivity values detected for the respective ferromagnetic metal objects to determine any difference found therebetween to an accuracy of at least 5 parts per million.

10. The method of claim 1 whereby residual stress in said ferromagnetic metal object is detected by very small changes in the electrical conductivity of said ferromagnetic metal object, changes formerly unobservable due to Barkhausen noise.

11. The method of claim 9 wherein a maximum magnetic field being generated with said probe device depends upon said magnetic permeability of said particular ferromagnetic metal object being tested.

12. The method of claim 11 wherein said maximum magnetic field being generated with said probe device does not exceed $10^{-3}$ Tesla.

13. The method of claim 9 wherein said test induction coil in said probe device is constructed with a surface configuration conforming to said particular surface of said ferromagnetic metal object being tested.

* * * * *